(12) United States Patent
El Achhab et al.

(10) Patent No.: US 9,114,256 B2
(45) Date of Patent: Aug. 25, 2015

(54) ELECTROSTIMULATION METHOD AND SYSTEM FOR THE TREATMENT OF SLEEP APNEA

(75) Inventors: El Bachir El Achhab, Madrid (ES);
Paula Maiumi Rubel, Madrid (ES);
Javier Montero Blasco, Madrid (ES);
Soraya Garcia Bustos, Madrid (ES);
Luis Cabezas Castillo, Madrid (ES)

(73) Assignee: TORYTRANS, S.L, Ciudad Real (ES)

( * ) Notice: Subject to any disclaimer, the term of this patent is extended or adjusted under 35 U.S.C. 154(b) by 0 days.

(21) Appl. No.: 14/375,710

(22) PCT Filed: Jan. 31, 2012

(86) PCT No.: PCT/ES2012/070060
§ 371 (c)(1),
(2), (4) Date: Sep. 24, 2014

(87) PCT Pub. No.: WO2013/113950
PCT Pub. Date: Aug. 8, 2013

(65) Prior Publication Data
US 2015/0018895 A1   Jan. 15, 2015

(51) Int. Cl.
| *A61N 1/36* | (2006.01) |
| *A61N 1/04* | (2006.01) |
| *A61B 5/08* | (2006.01) |
| *A61B 5/00* | (2006.01) |

(52) U.S. Cl.
CPC ............ *A61N 1/3601* (2013.01); *A61N 1/0484* (2013.01); *A61N 1/36014* (2013.01); *A61B 5/0826* (2013.01); *A61B 5/4818* (2013.01)

(58) Field of Classification Search
None
See application file for complete search history.

(56) References Cited

U.S. PATENT DOCUMENTS

| 4,982,738 | A  | * | 1/1991 | Griebel ................ 600/483 |
| 5,245,995 | A  |   | 9/1993 | Sullivan |
| 5,275,159 | A  | * | 1/1994 | Griebel ................ 600/324 |
| 6,345,202 | B2 |   | 2/2002 | Richmond |
| 6,881,192 | B1 | * | 4/2005 | Park .................... 600/529 |
| 7,404,799 | B1 | * | 7/2008 | Koh .................... 600/484 |
| 2005/0081847 | A1 | * | 4/2005 | Lee et al. ............ 128/200.24 |
| 2006/0145878 | A1 |   | 7/2006 | Lehrman |
| 2008/0021506 | A1 |   | 1/2008 | Grocela |
| 2010/0048985 | A1 |   | 2/2010 | Henke |
| 2010/0076323 | A1 |   | 3/2010 | Shrivastav |

FOREIGN PATENT DOCUMENTS

| WO | 0213677 A2 | 2/2002 |
| WO | 2006054359 A1 | 5/2006 |
| WO | 2008098365 A1 | 8/2008 |
| WO | 2010054481 A1 | 5/2010 |
| WO | 2011010384 A1 | 1/2011 |

* cited by examiner

*Primary Examiner* — Kennedy Schaetzle
(74) *Attorney, Agent, or Firm* — Lucas & Mercanti, LLP

(57) ABSTRACT

Electric stimulation method and system for treating Obstructive Sleep Apnea (OSA) Syndrome using an external actuator on the pharyngeal-laryngeal muscles.

Using this actuator, the muscles involved receive an electric stimulus, with the aim of widening the muscular opening and attaining sufficient air flow to prevent the lack of air. Said stimulus only acts in the event of an apnea episode being detected, by means of analyzing sound patterns of the upper airways. Both detection and treatment arc self-regulatory, in order to adapt to the patient's morphology and the evolution of the condition or problem.

9 Claims, 4 Drawing Sheets

ELECTROSTIMULATION METHOD AND SYSTEM FOR THE TREATMENT OF SLEEP APNEA

CROSS-REFERENCE TO RELATED APPLICATIONS

This application is a 371 of PCT/ES2012/070060 filed Jan. 31, 2012, which is incorporated by reference herein.

FIELD OF THE INVENTION

The present invention relates to muscular stimulation, specifically stimulation using adjustable electrical signals in order to treat episodes of insufficient breathing produced during Obstructive Sleep Apnea (OSA) Syndrome.

BACKGROUND OF THE INVENTION

Various epidemiological studies have proven that sleep apnea is highly prevalent amongst sleep related conditions and affects between 4-6% of males and 2-4% of females in the general middle-aged adult population.

The main problems related to sleep apnea include significant reduction in quality of life, arterial hypertension and the development of cardiovascular and cerebrovascular diseases.

Obstructive sleep apnea is therefore one of the most widespread and worrying sleep conditions.

The most extensive methods known to date for treating obstructive sleep apnea include:

US005245995A: A device named CPAP, consisting of a turbine that transmits a predetermined pressure via a nasal mask, adapted to the subjects face and fixed with a harness, with which the circuit is closed.

The device is effective in terms of continuously treating the illness, however presents various limitations:

Nasal congestion and/or obstruction. Nasal congestion is the most common and treatment depends on the cause behind it. It usually arises as a result of edema and inflammation of the nasal mucus.

Irritated skin. This occurs in the area that comes into contact with the CPAP mask.

A dry throat. This is caused by water being lost from the soft palate, as a result of snoring and apnea and the air flow from the device itself. In order to be corrected, it is necessary to install a humidifier/heater connected to the CPAP.

Noise. In addition to noise produced by the CPAP, which goes unnoticed after the first few weeks, patients and their companions complained of tonality changes between inhalation and exhalation produced in the mask.

Cold. This is particularly significant in cold areas and houses without heating, where in winter, air from the CPAP may enter the VAS at 15° C. or lower (the temperature recommended for sleep being around 19° C.).

Surgical techniques: these involve generally aggressive surgical techniques, which are reserved in many cases for when the CPAP does not work or for patients who reject it before looking into it further. It requires very precise prior anatomical exploration and must be carried out by experienced surgeons. The ill person must be informed of the chances of success exhaustively and may require more than one intervention.

Electric stimulation: The first research on electric stimulation treatments for obstructive sleep apnea was carried out in the 1980s, when Dr. Miki's team in Japan carried out various experiments on this usage.

Since then, several pieces of apparatus have been produced, which have attempted to apply principles related to electric stimulation in order to prevent the collapse of the upper airways by means of contracting the muscles involved. Some are internal, whilst others are external.

One device implanted into the subject internally is:

US006345202B2, which proposes a method for treating apnea using micro-electrodes implanted into strategic places inside a patient. They are controlled wirelessly by an external transmitter, in order to stimulate the muscular and nerve tissue in a constructive way, which helps to open the airways blocked.

External Devices include:

US 2008/0021506A1, which uses electrodes fitted to the surface, to prevent snoring and sleep apnea.

US 2006/0145878A1, which proposes a method and system for fighting apnea, wherein the subject is woken up.

WO 2006/054359, which proposes electrical timulati by means of applying electrodes in the jaw portion of a patient, in order to prevent sleep apnea. It therefore applies electrical signals repeatedly during the night, without considering the state of obstruction in the upper airways.

One limitation common to all the above proposals is the lack of regulation. They do not facilitate automatic adjustment, in order to adapt to the morphological characteristics and the intensity level of apnea episodes of each patient.

The same goes for the CPAP device, wherein prior adjustment is required, thus increasing the costs of installing the apparatus for each patient considerably. It is currently substituted by an automatic graduation CPAP system known as the APAP (Roldán N et al. 2008).

The apparatus and method described below compensates for the deficiencies identified in the state of the art and constitutes a significant technological advancement, since it facilitates self-regulating detection and treatment, in order to adapt to a patient's morphology. It uses the minimal electric shock required in terms of both frequency and intensity in the muscles involved. Furthermore, it facilitates follow-up and control of the evolution of the condition.

DESCRIPTION OF THE INVENTION

The invention is particularly suited for the continuous treatment of sleep and respiratory conditions, by means of self-regulating electrical stimuli, in order to adapt to a patient's type set.

The invention makes it possible to process and store information relative to apnea episodes and electric stimulation, in addition to making it possible to adjust the electrical stimuli in order to adapt to the evolution of the condition or problem. In turn, it makes it possible to follow-up over time in order to assess a patient's prowess.

Muscular stimulation is carried out cutaneously on the patient's neck, without secondary side effects or alterations to sleep settings. It therefore acts on the muscles involved in the collapse of respiratory airways successfully.

The effect of stimulating muscles additionally serves to train and strengthen those responsible for keeping the upper airways open (the genioglossus).

The invention is preferably built in such a way that it is portable and may be easily transported. Patients may therefore take it with them and use it both in their usual home environment and in other situations (for example during travel).

The invention includes a neck piece and a central device. The neck piece in turn comprises an electronic support, responsible for collecting the signal from the upper airways and transmitting electrical impulses, in addition to an elastic band, designed in an anatomical format, which is molded to the patient's neck.

The device has an apnea detection module based on processing the acoustic signal produced by the upper airways. It is therefore possible to adjust detection criteria to the optimal breathing thresholds of each patient, within a continuous learning process. The signal produced in the respiratory airways is processed to calculate the strength thereof. In turn, a number of thresholds are defined, between which the strength must be situated. In the event of the strength being below the threshold linked to breathing, the duration thereof is thereby counted. If this duration exceeds another time threshold, it is concluded that there is a period of apnea and this result is communicated to the actuation module.

The actuation module controls the electric stimulator and facilitates the self-regulation of the intensity and frequency of electrical stimulus, according to the characteristics of the episode and patient. It is ensured that the stimulus is enough for each patient's layer of adipose tissue and for the severity of the collapse in the airways. A stimulus is therefore generated at a specific intensity and frequency.

The device may store information relating to apnea episodes and the electrical stimuli in a memory (external, if necessary), thus creating a time sequence that facilitates the automatic assessment of the evolution of sleep apnea and modification of the electric stimulation program, in order to adjust the intensity and/or frequency of the electrical stimulus to be applied.

The device may include a communication system, by means of a cable or wireless, which makes it possible to connect to an external device. Said external device may in turn be in charge of other functions, for example, producing a report on the evolution of the apnea episodes.

BRIEF DESCRIPTION OF THE DRAWINGS

FIG. 2. (b) represents the components of the neck piece (10) in detail.

FIG. 2. (c) is a detailed view of the means used to fasten the neck piece (10).

A neck piece (10) with free electrodes to be placed in the submental area of the muscles in order to facilitate electric stimulation and a microphone in contact with the neck area, in order to receive the sound of the air flow crossing the upper airways. Central device (20) with a module for processing acoustic signals, electric stimulation. and the controller thereof, a battery and preferably an external memory. The sound signal is received from the microphone and processed and where necessary, the electrical signal is transmitted to the electrodes connected to the neck piece (10).

Figure 4:
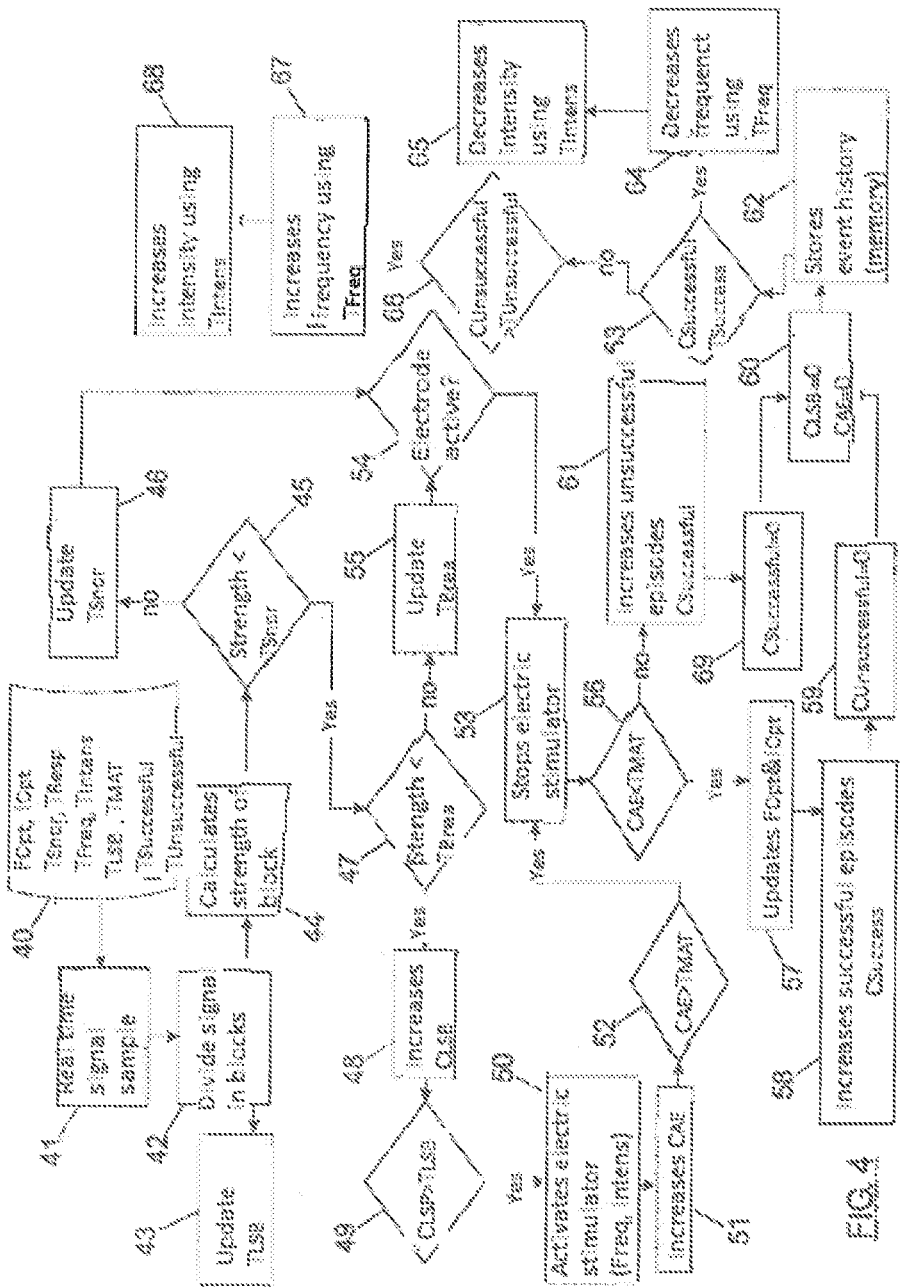

FIG. 4. is a flow diagram of one embodiment.

PREFERRED EMBODIMENTS

The design of the device makes it comfortable to wear for the whole night, without disturbing normal sleep cycles, with a microphone fitted in such a way that it comes into contact with the neck and two electrodes, which are placed in a submental position.

A small, central device (usually placed on the chest), with an apnea episode detection module based on analyzing the acoustic signal of the upper respiratory airways and an electric stimulation actuator, capable of producing a variable electrical signal, in terms of both intensity and frequency. Furthermore, there is close communication between both modules, in such a way that controlled feedback is produced between the electrical signal applied to the muscles and the duration of the apnea episodes.

Below is a description of an exemplary embodiment of the invention, with reference to the figures.

Figure 1:
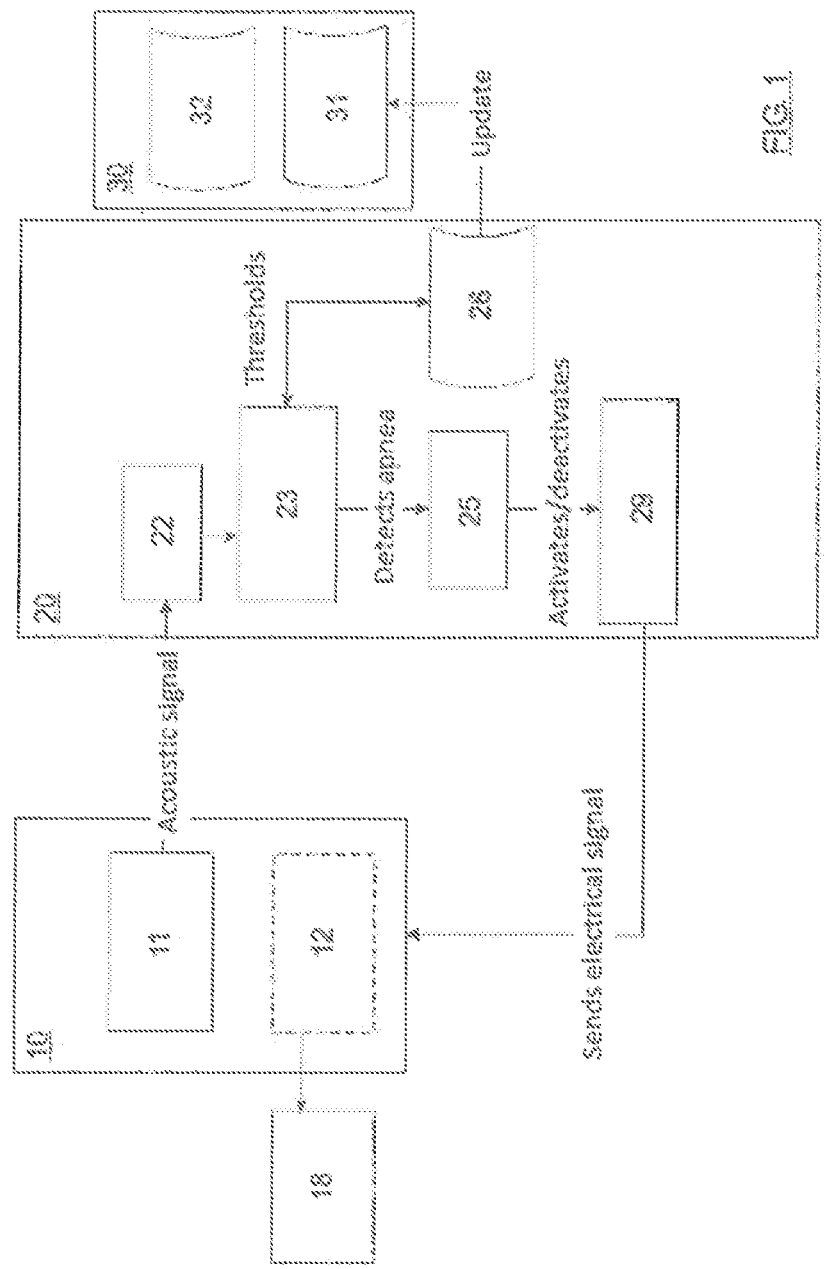
FIG. 1. is a schematic block diagram of an electric stimulation system used to treat OSA, according to the present invention. The main components are shown.

According to FIG. 1, the system for treating apnea comprises two modules: a neck piece (10) and a central device (20). It may also include a user interface (32) used to communicate with an external device (30) responsible for storing information of interest in a database (31) or for recovering data (history of apnea episodes) stored in the memory (26) of the central device (20) for subsequent follow-up and study of the evolution of the condition.

The neck piece (10) in turn comprises a microphone (11) adjusted to capture the sound of the upper airways. Furthermore, it preferably has two terminals (12) in order to connect the electrodes (18) that may be extracted and replaced in order to stimulate the muscles involved in the apnea.

The microphone (11) collects the acoustic signal of the upper respiratory airways generated by the patient in real time.

The electrodes (18) may be easily coupled to their adaptors (12) and are preferably flexible in order to adjust to various neck anatomies correctly.

The central device (20) incorporates a signal processer (23) for treating the acoustic signal coming from the microphone (11) and a method for detecting apnea episodes. The central device (20) receives the pre-filtered analogue signal, converts it into a digital signal and may furthermore include a filter (22) to be used on the digital signal, in order to reduce harmful noises.

The processing unit (23) recognizes an apnea episode when the strength of the acoustic signal falls below a certain strength threshold during a minimum period of time, It then decides to send a signal to the electric stimulator (25) controller. In turn, the controller (25) recovers the optimal frequency and intensity values previously adapted for the current episode, in such a way that it always administers the smallest shock necessary in order to stop an apnea episode. It then activates the electric stimulator (29), which in turn generates the electric shock to the electrodes (18). At the end of each stimulation, the processing unit (23) checks whether or not the apnea episode has been successfully corrected. Moreover, they are stored in a memory (26), which is external if necessary, providing a record of said episodes.

The patient may connect the apparatus to an external device (30) on a daily basis using a cable (15) (for example of the USB variety) and a specific user interface program (32) to download data from the external data base (31) and collect the data in order to create sleep apnea treatment follow-up reports, amongst other tasks.

Figure 2A:
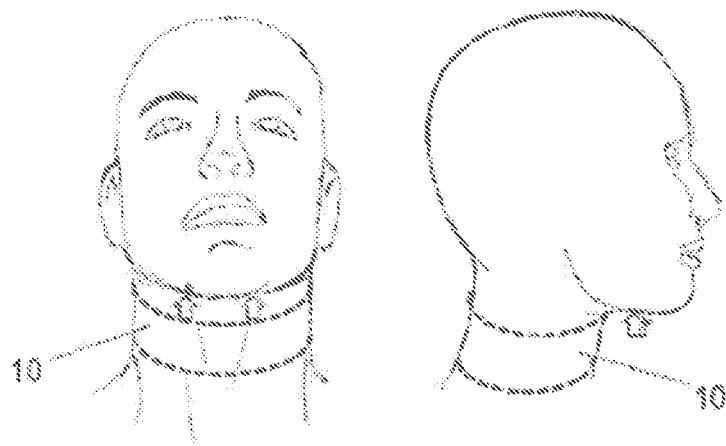
FIG. 2. (a) is an example of a neck piece (10) fitted around a patient's neck.
Figure 2B:
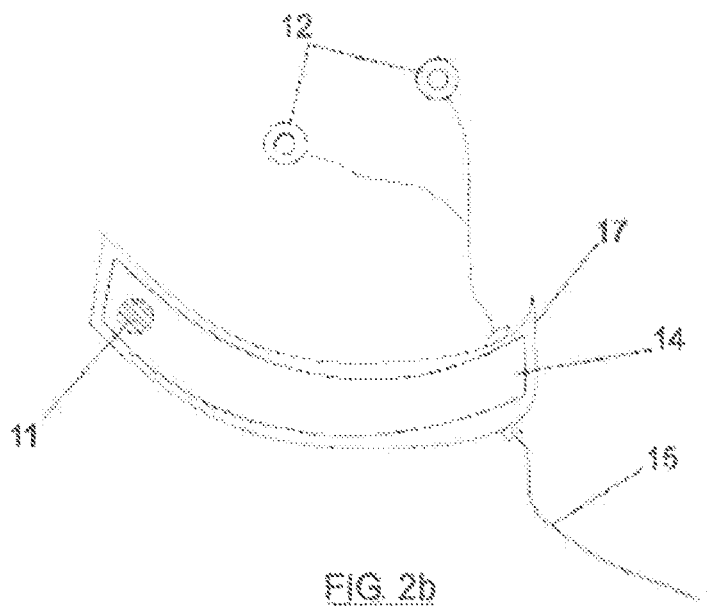
Figure 2C:
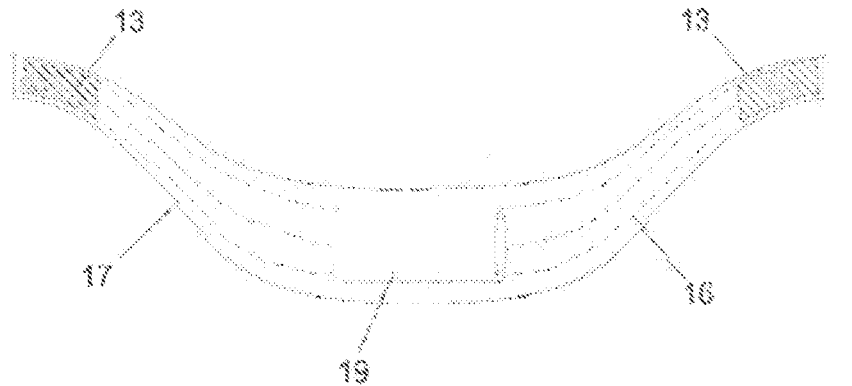

As can be observed in FIG. 2, the ergonomic support (14) of the neck piece (10) may be made of a semi-rigid material, Which may be shaped and adapted to the neck (for example, aluminum). This would contain the electronic portion. The inside may be covered with polyurethane foam. The microphone (11) is also incorporated into the internal portion of the support, preferably at one side and may be protected with a sponge against the air and reduce unwanted external noises.

The electronic support (10) may contain two terminals (12), wherein he replaceable electrodes (18) are connected.

The electronic support of the neck piece (10) may be coated with a textile material (17), which is preferably hypoallergenic, resistant to dust mites, porous, ergonomic and breathable, as well as being easy to wash, In the external portion of the electronic support (10), a Velcro coating (13) may form an easy fasten system.

In turn, the electronic support (10) may be shaped to the patient's neck by means of an elastic band with silicone straps (16) in order to provide a non-slip fit. The band is designed in an anatomical format that is shaped to the patient's neck. The electronic support (10) is joined to the band by means of a Velcro easy fasten system or pocket. In the external portion of the band, a Velcro coating (13) may serve as a closure.

Figure 3:
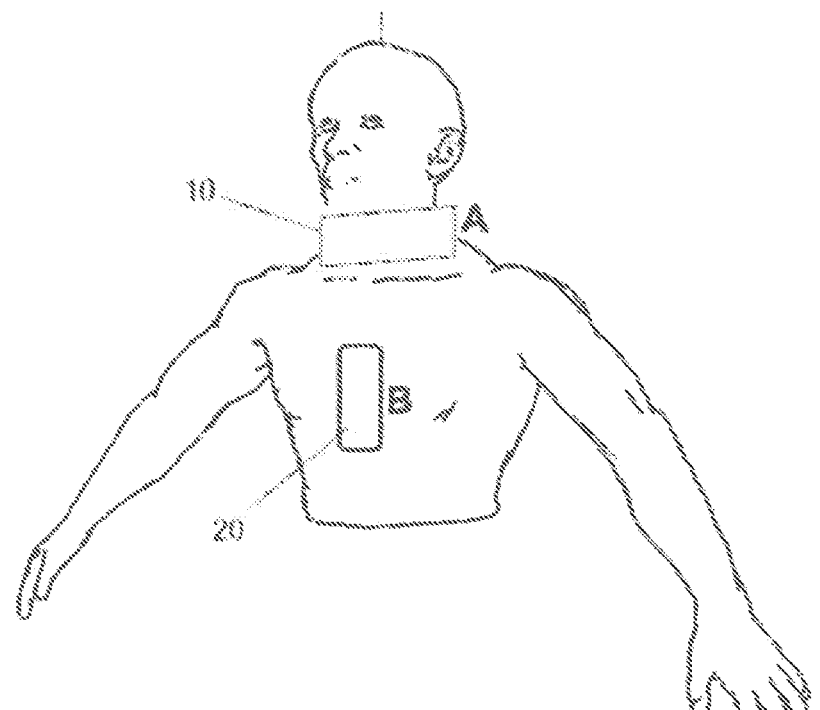
FIG. 3. shows how the elements of the neck piece (10) and central device (20) of the system are placed on a patient's body.

FIG. 3 shows the elements that form the piece of equipment for treating apnea, namely the neck piece (10) and the electric stimulator module (20) on the patient's neck.

The neck piece (10) leaves the electrodes (18) free in order to place them in the submental area for electric stimulation alongside a microphone (11) in contact with the area of the neck for receiving the sound of the air flow crossing the upper airways.

The central device (20) is formed by a digital signal processor (23), an electric stimulator (29), a controller (25) for the same, an external memory (26) if required and a battery.

The sound signal coming from the microphone (11) reaches the processor (23). The electronic impulses are transmitted from the central device (20) to the electrodes (18) placed in the patient's submental region.

Subsequently, FIG. 4 describes the intelligence of the system in the apnea episode detection and treatment method using variable electronic impulses issued by the processor (23). Upon the device (20) starting up, the processor (23) recovers the optimal thresholds and settings, if necessary, from the external memory (26), updating them in a volatile memory. The first time the device (20) is used, said thresholds and settings are defined at a default value, the same being adjusted to their optimal operational value with each use, according to the conditions and characteristics of the patient and their illness.

The processing unit (23) receives the voice signal in real time, divides it into blocks of a pre-established size and calculates the strength of each block. In turn, blocks of said signal are stored so that when a minimum value is reached, the self-correlation thereof is calculated, provided that said blocks do not contain apnea episodes. The self-correlation function provides information on the period in which the signal was issued, thus making it possible to update the threshold for low strength blocks ($T_{LSB}$), which shall serve as one of the criteria for detecting apnea.

When the strength of the current block exceeds the snoring threshold ($T_{Snor}$) this is because the patient is snoring. It therefore updates the $T_{Snor}$ threshold, adjusting it to the patient's snoring characteristics.

In contrast, if the strength falls below the $T_{Snor}$ threshold and in turn, above the breathing threshold ($T_{Brea}$), this is because the patient is breathing. It therefore updates the $T_{Brea}$ threshold, adjusting it to the patient's breathing patterns.

In the opposite case, if the strength falls below the $T_{Brea}$, it indicates that an apnea episode has begun. In order to be sure of this, it starts to count the number of low strength blocks ($C_{LSB}$), which indicates the time in which the patient has gone without breathing.

When this time $C_{LSB}$ exceeds the maximum threshold of low strength blocks ($T_{LSB}$), it recognizes an apnea episode and therefore sends a signal to the controller (25), in order to activate the electric stimulator (29) using the current frequency and intensity values of the processor.

Once the electric stimulator (29) has been activated, it starts to count the time ($C_{AE}$) in which it is active.

The processor sends an order to the controller to stop the electrical stimulator in one of the following two cases: if the active electrode counter $C_{AE}$ exceeds the maximum activation time threshold ($T_{MAT}$) or if breathing or snoring is detected.

At the end of each stimulation, the processor (23) checks Whether or not the apnea episode has been corrected successfully. This is confirmed when the electrode activation time is lower than the maximum activation time. The counter of successful cases ($C_{Successful}$) is also increased and the unsuccessful cases counter ($C_{unsuccessful}$) is set to zero. If it failed, the unsuccessful cases counter ($C_{Unsuccessful}$) is thus increased and the successful cases counter ($C_{Successful}$) is set to zero.

Finally, the $C_{LBP}$ and $C_{AE}$ variables are restarted and the apnea event is stored in the events record found in a memory (26).

The signal processing unit (23) then decides to reduce the frequency and intensity values once the number of successful cases has exceeded the successful cases threshold ($T_{Successful}$). In the event of the opposite, it increases the frequency and intensity values once the number of unsuccessful cases has exceeded the unsuccessful cases threshold ($T_{Unsuccessful}$), always administering the smallest shock required to stop an apnea episode.

Before turning the device off, the processor (23) stores the breathing thresholds and electrical impulse settings adjusted to the patient in the memory (26), in order to provide optimal operation the following night.

The processor (23) therefore adapts both the breathing thresholds ($T_{Snor}$ and $T_{Brea}$), depending on the strength of the sound captured and the period of the signal ($T_{LSB}$), depending on the patient's breathing rate, i.e. the number of times the patient breathes or snores per minute. Said thresholds therefore vary depending on a patient's behavior, the precision of the detection of an apnea episode improving as they are adapted.

Abbreviations
$T_{LSB}$ low strength blocks threshold
$T_{Snor}$ snoring threshold
$T_{Brea}$ breathing threshold
$T_{Free}$ electric stimulator frequency threshold
$T_{Intens}$ electric stimulator intensity threshold
$N_{LSB}$ number of low strength blocks
$C_{AE}$ active electrode counter
$T_{MAT}$ minimum activation time threshold
$C_{Successful}$ successful cases counter
$F_{Opt}$ optimal frequency values
$I_{Opt}$ optimal intensity values
$C_{Unsuccessful}$ unsuccessful cases counter Numerical References
10 Neck piece.
11 Microphone.
12 Electrode terminals.
13 Velcro.
14 Ergonomic support.
15 Cable.
16 Silicone strips.
17 Textile material.
18 Electrodes.
19 Pocket for storing electronic support 10.

20. Central device.
22 Filter.
23 Processing unit.
25 Controller.
6 Central device 20 memory.
29 Electric stimulator.
30 External device.
31 External database.
32 User interface.
40 Load thresholds: $F_{Opt}$, $I_{Opt}$, $T_{Snor}$, $T_{Brea}$, $T_{Frec}$, $T_{Intens}$, $T_{LSB}$, $T_{MAT}$, $T_{Successful}$ $T_{Unsuccessful}$.
41 Real time sample of the signal.
42 Divide the signal into blocks.
43 Update $T_{LSB}$.
44 Calculate the strength of the block.
45 Check strength is lower than $T_{Snor}$.
46 Update $T_{Snor}$.
47 Check strength is lower than $T_{Brea}$.
48 increase $C_{LSB}$.
49 Check $C_{LSB}$ is greater than $T_{LSB}$.
50 Electric stimulator activation.
51 Increase $C_{AE}$.
52 Check $C_{AE}$ is greater than $T_{MAT}$.
53 Stop the electric stimulator 29
54 Check the electric stimulator 29 is active.
55 Update $T_{Brea}$.
56 Check $C_{AE}$ is lower than $T_{MAT}$
57 Update $F_{Opt}$, $I_{Opt}$ of the electric stimulator 29
58 Increase $C_{successful}$,
59 Restart $C_{Unsuccessful}$ counter=0
60 Restart $C_{LSB}$=0, $C_{AE}$=0
61 Increase $C_{Unsuccessful}$ counter
62 Store event records
63 Check $C_{Successful}$ is greater than $T_{Successful}$
64 Decrease frequency using $T_{Free}$
65 Decrease intensity using $T_{intens}$
66 Check $C_{Unsuccessful}$ is greater than $T_{Unsuccessful}$
67 Increase frequency using $T_{Free}$
68 Increase intensity using $T_{intens}$
69 Restart the $C_{Succesful}$ counter=0

The invention claimed is:

1. An electric stimulation system for treating sleep apnea in a patient, comprising:
   treatment means designed to treat the acoustic signal generated by the patient's breathing and divide it into a plurality of blocks, each block corresponds to a fragment of the acoustic signal within a time interval,
   said treatment means are furthermore designed to measure the strength of a plurality of blocks of the acoustic signal;
   control means designed to count, in the plurality of blocks measured, the number of low strength blocks $C_{LSB}$ when the strength of the block is less than a strength threshold linked to breathing, $T_{Brea}$, said control means furthermore being designed to determine the existence of an apnea episode when the number of low strength blocks $C_{LSB}$ exceeds a threshold on the number of low strength blocks $T_{LSB}$,
   said control means are also designed to selectively control, if there is an apnea episode, the activation of a number of electric stimulation means, designed to apply an electric signal to the submental muscles linked to the respiratory airways.

2. The system according to claim 1, wherein the blocks are generated by the treatment means, after having sampled and filtered the acoustic signal.

3. The system according to claim 1, wherein the low strength block threshold $T_{LSB}$ is estimated by the control means in coordination with the treatment means, with said threshold being linked to the number of blocks present in the acoustic signal generated by the patient's breathing in a breathing interval.

4. The system according to claim 1, wherein the electric stimulation means start a temporary counter that measures the activation time, $C_{AE}$, in such a way that if it exceeds a maximum activation limit $T_{MAT}$, the control means deactivate the electric stimulation means independently of the existence of the apnea episode.

5. The system according to claim 4, wherein if the control means still determine the existence of the apnea episode, they increase an unsuccessful episode count $C_{unsuccessful}$.

6. The system according to claim 4, wherein if the control means still determine the non-existence of an apnea episode, they increase a successful episodes count, $C_{Successful}$.

7. The system according to claim 4, wherein the control means adjust the value of the frequency and/or intensity of the electrical signal generated by the electric stimulation means, in such a way that:
   the intensity and/or frequency is decreased within a range depending on the value of the $C_{Successful}$ count and
   the intensity and/or frequency is increased within a range depending on the value of the $C_{Unsuccesful}$ count.

8. The system according to claim 1, wherein the treatment means are configured to receive the signal from a microphone designed to capture the acoustic signal generated by the patient during breathing.

9. The system according to claim 1, wherein it furthermore comprises storage means, designed to store at least one of the following values:
   $T_{Brea}$, $T_{LSB}$, $C_{AE}$, $T_{MAT}$, $C_{Unsuccessful}$, $C_{Successful}$, $C_{LSB}$, maximum and minimum frequency range for the electrical signal applied, maximum and minimum intensity range for the electrical signal applied.

* * * * *